(12) United States Patent
Torrance et al.

(10) Patent No.: US 7,674,272 B2
(45) Date of Patent: Mar. 9, 2010

(54) BEARING SYSTEM TO SUPPORT A ROTATABLE OPERATING HEAD IN AN INTRACORPOREAL DEVICE

(75) Inventors: Casey Torrance, Seattle, WA (US); Edward I. Wulfman, Woodinville, WA (US); Matt Hefner, Fall City, WA (US)

(73) Assignee: Pathway Medical Technologies, Inc., Kirkland, WA (US)

( * ) Notice: Subject to any disclaimer, the term of this patent is extended or adjusted under 35 U.S.C. 154(b) by 1183 days.

(21) Appl. No.: 10/760,759

(22) Filed: Jan. 20, 2004

(65) Prior Publication Data

US 2004/0181249 A1    Sep. 16, 2004

Related U.S. Application Data

(60) Provisional application No. 60/453,846, filed on Mar. 10, 2003.

(51) Int. Cl.
*A61B 17/32* (2006.01)
(52) U.S. Cl. .................. 606/170; 606/171; 606/180; 600/141; 600/142; 604/528
(58) Field of Classification Search .............. 606/139, 606/140, 142, 144, 148, 166–180, 206, 205; 600/141, 142, 146, 585; 604/95.01, 95.03, 604/95.04, 528
See application file for complete search history.

(56) References Cited

U.S. PATENT DOCUMENTS

| 4,432,349 | A | * | 2/1984 | Oshiro ..................... 600/141 |
| 5,209,747 | A | * | 5/1993 | Knoepfler .................. 606/16 |
| 5,312,427 | A | | 5/1994 | Shturman |
| 5,330,502 | A | * | 7/1994 | Hassler et al. .............. 606/205 |
| 5,350,391 | A | * | 9/1994 | Iacovelli .................... 606/170 |
| 5,374,277 | A | * | 12/1994 | Hassler ..................... 606/207 |
| 5,383,888 | A | | 1/1995 | Zzenyatsky et al. |
| 5,405,344 | A | * | 4/1995 | Williamson et al. ............ 606/1 |
| 5,540,706 | A | * | 7/1996 | Aust et al. .................. 606/170 |

(Continued)

FOREIGN PATENT DOCUMENTS

FR    2 730 020 A3    8/1996

(Continued)

*Primary Examiner*—Darwin P Erezo
(74) *Attorney, Agent, or Firm*—Ann W. Speckman; Janet Sleath; Speckman Law Group PLLC (57) ABSTRACT

A bearing system useful in an intracorporeal device connects an operating head, a rotatable drive shaft and a catheter. The bearing system includes a static member in fixed communication with the distal end of the catheter, an interior shaft that is in rotatable communication with the drive shaft and the operating head, and at least one connecting structure. The static member has at least one opening through which the connecting structure moveably rests against a seat of the interior shaft. The position of the connecting structure within the seat enables the bearing to accept a rotational load of the rotating drive shaft and/or thrust load in the direction of the longitudinal length of the catheter. The connecting structure further retains the internal shaft and static member of the bearing system. A clearance space between the internal shaft and the catheter may permit the interior shaft to tilt relative to the catheter and flexibly orient the operating head at different angles about longitudinal axis of the catheter.

17 Claims, 11 Drawing Sheets

U.S. PATENT DOCUMENTS

| | | | |
|---|---|---|---|
| 5,549,637 A * | 8/1996 | Crainich | 606/207 |
| 5,643,294 A * | 7/1997 | Tovey et al. | 606/148 |
| 5,752,973 A * | 5/1998 | Kieturakis | 606/207 |
| 5,792,165 A | 8/1998 | Klieman et al. | |
| 5,972,012 A | 10/1999 | Ream et al. | |
| 6,258,109 B1 | 7/2001 | Barry et al. | |
| 6,331,078 B1 | 12/2001 | Van Duyn | |
| 6,565,588 B1 | 5/2003 | Clement et al. | |
| 6,913,613 B2 * | 7/2005 | Schwarz et al. | 606/206 |
| 2002/0007190 A1 | 1/2002 | Wulfman et al. | |
| 2004/0006358 A1 | 1/2004 | Wulfman et al. | |

FOREIGN PATENT DOCUMENTS

| | | |
|---|---|---|
| JP | 3 030 522 U | 8/1996 |
| JP | 10-016585 | 1/1998 |

* cited by examiner

BEARING SYSTEM TO SUPPORT A ROTATABLE OPERATING HEAD IN AN INTRACORPOREAL DEVICE

CROSS-REFERENCE TO RELATED APPLICATION(S)

This application claims priority from U.S. Provisional Patent Application No. 60/453,846, filed Mar. 10, 2003, the contents of which are incorporated herein by reference in its entirety.

FIELD OF THE INVENTION

The present invention relates to a bearing system for an operating head that is rotatable in an intracorporeal device and particularly relates to a bearing system for connecting the operating head and a drive shaft in the intracorporeal device.

BACKGROUND OF THE INVENTION

In the medical field, it is often required that a medical practitioner manipulate an intracorporeal device within a body cavity of a patient. The device may be used for therapeutic or diagnostic purposes. Sometimes, the device includes an elongated drive shaft extending through a catheter and leading to an operating head at the distal end of the device. The drive shaft may rotate and thereby rotate the operating head. In addition to the drive shaft, the catheter may also include a guide wire, conduit, protective sheath, etc.

A general challenge in using an operating head is that it is often difficult for the operating head to reach the area of interest. The intracorporeal device must usually be routed along a tortuous path, through various internal structures within the body before arriving at the target site. For example, an obstructed blood vessel may be located in peripheral vessels, coronary vessels, cranial vessels, or other areas. In order to be directed through sharp bends in the path to the target site, such as sharp bends in blood vessels, it is desirable for the device to be as flexible as possible and allow the operating head to be directed at various angles relative to the longitudinal axis of the drive shaft and catheter. Moreover, the requisite small size of components required to be translated through vessels may limit performance of the device.

Furthermore, once the operating head is located at the site of interest, it is sometimes difficult to place the operating head into the appropriate operating position relative to the target site, e.g. an obstruction. The target site may be located in various places in a body cavity, such as along the walls of a lumen, e.g. a blood vessel. In addition, the operating head often needs to be operated within small confines of the interior body cavity. Accordingly, it would facilitate placement and operation of the operating head if the device was flexible such that the operating head could be oriented at various angles within the body cavity.

In intracorporeal devices in which an operating head attaches to a drive shaft, the drive shaft and catheter provide at least some flexibility along the lengths of the drive shaft and catheter in order to move the device within the body. However, flexibility of the device is usually compromised in the area where the drive shaft is fixed to the operating head at the distal end of the device. In most systems, the drive shaft is fixed to the operating head to translate rotational torque from the drive shaft to the operating head. Furthermore, the catheter must have a mechanism to support the rotating operating head. As a result of the hardware require to couple the operating head to the drive shaft and fixed catheter, the operating head may have limited ability to reach and access the target site.

Moreover, any flexibility provided for the operating head, e.g. tilting, must also occur within a controllable range of angles. Where an operating head is allowed to freely move or pivot, the operating head may be excessively collide with beneficial material, such as a vessel wall or a stent, causing damage to beneficial material.

Existing intracorporeal devices generally do not provide effective flexibility of the operating head at the junction between the drive shaft and operating head. Some prior systems use one or more gears and pins to pivot the operating head. Various of these devices are described in U.S. Pat. Nos. 5,792,165 and 5,383,888. Examples of such devices have a cutting portion with two pieces that come together to snip or pinch the unwanted matter. The cutting portion pivots about a pin by engaging gear teeth. However, operation of this gear-type of bearing system would result in high friction if the operating head were rotated at high speeds. Furthermore, some applications, e.g. cutting systems used in the vasculature system, require a very small cutting head, but it is difficult to design such a miniscule intracorporeal device using the gear-type bearing system.

A further challenge of designing high performance and reliable intracorporeal devices is that the devices are often subject to a variety of forces that can create strain on device components. For example, a force is created when the operating head contacts target matter and the device is subjected to a thrust load along direction of the length of the device. In addition, where the operating head rotates, the device is subject to rotational forces. At the same time, the distal components of intracorporeal devices need to be small in order to be manipulated within a small body pathways and cavities, e.g. lumens. The small components are more vulnerable to damage from heavy loads. It is essential for the device to be able to absorb the loads during an operation without having its components wear down and fail while in use.

An additional challenge of distal components of the operating head is that channels are sometimes required to aspirate or infuse liquid, blood or materials from or to the site of operation. Thus, flexibility of the operating head must not restrict flow through the device.

It is therefore desirable to provide a system for mounting an operating head to a drive shaft and catheter that provides flexibility at the operating head for easy manipulation within a body. The system should allow for controlled tilting of the operating head with respect to the catheter and/or drive shaft. It is further desirable for the mounting system to have small dimensions and support radial and/or thrust loads experienced during rotation and operation of the device. It would be further advantageous for the system to provide for aspiration or infusion of fluids or materials. The present invention fulfills these needs and provides further related advantages.

SUMMARY OF THE INVENTION

The present invention provides a miniature bearing system for coupling a small distal rotating operating head to a drive shaft and static catheter in an intracorporeal device. The bearing system provides a means for flexibility at the connection that joins the operating head, drive shaft and catheter, and also provides a channel for aspiration or infusion of fluids of material through the bearing system. Furthermore, the bearing system supports rotational, axial and/or thrust forces and also provides for flexibility at the junction of the operating head, drive shaft and catheter. The bearing system comprises an internal shaft in rotatable communication with both the drive shaft that extends within the catheter and the operating head. The bearing system further comprises a static member as an outer sleeve in fixed relationship with the catheter and surrounding an enclosed portion of the internal shaft. The internal shaft and static member are engaged by one or more connecting structures, such as rods, at least a portion of each rests through an opening in the static member and onto a seat of the internal shaft. The components of the bearing system are generally very small, e.g. micron range, in order to accommodate small structures of the body.

During use of the device, the drive shaft, internal shaft of the bearing system and operating head are rotated as a unit, whereas the catheter and static member of the bearing system form a separate unit that is in a stationary position during rotational action of the drive shaft and operating head. The internal shaft is capable of orienting the operating head about a longitudinal axis relative to the catheter. During operation, the internal shaft tilts about the connecting structure(s) and pivots within a clearance gap between the internal shaft and the device component(s) that encase the proximal portion of the internal shaft, such as the catheter and/or static member. As the internal shaft tilts, the connecting structure(s) contact (s) the internal shaft at various points on the seat. In this manner, the connecting structure(s) act(s) as a bearing surface and permits the internal shaft to be movably coupled to the static member.

The static member typically comprises at least one opening that may be in a recessed indentation for accepting a connecting structure. In one embodiment, the indentation may have two opposing longitudinal raised ends for retaining one connecting structure in each indentation. The raised ends of the recessed openings may be coupled to the ends of the connecting structure(s) and prevent(s) the connecting structure(s) from being pushed entirely through the opening. A contact portion each connecting structure is received by the seat of the internal shaft. This contact between the connecting structure and the seat retains the static member with respect to the internal shaft.

Typically the connecting structure(s) and seat comprise materials that are of differing hardness. For example, the connecting structure(s) often comprise(s) cold drawn stainless steel and the seat comprises a material harder than the connecting structure, such as titanium nitride. In another example, the seat comprise(s) cold drawn stainless steel and the connecting structure(s) comprises a material harder than the seat, such as titanium nitride. The different connecting structure and seat materials permit the bearing system to be consistently reliable, even under high operational forces and resist wear during its use.

In one embodiment, the bearing system may include contact points between the distal ends of the internal shaft and static member to meet during tilting of the operating head to a specific angle, thus limiting the angle of tilt. For example, the contact point of the internal shaft may include a contact surface and the contact point of the static member may include a stop.

In some embodiments the maximum tilt angle of tilt may be limited by the configuration and/or placement of the stop of the static member meeting the contact surface of the internal shaft; the arrangement of the seat of the internal shaft relative to the connecting structures; and/or the configuration, depth and/or placement of the clearance gap in which the internal shaft may pivot. For example, the operating head may tilt to an angle limit between about 5 to 20 degrees with respect to the longitudinal axis of the catheter. Often, the operating head may be provided with an angle limit between about 10 to 20 degrees, and more particularly about 10 degrees. However, other angle limits are possible and intended within the scope of the present invention.

In still another embodiment, the internal shaft may further be provided with at least one port through which fluid may be infused and/or aspirated. A lumen extending through at least a portion of the device may permit passage of fluid or material.

BRIEF DESCRIPTION OF THE DRAWINGS

These and other embodiments of the present invention are described in detail below and illustrated in the drawings, in which:

FIGS. 3A and 3B show one embodiment of a bearing system of the present invention in an intracorporeal device, wherein

FIGS. 4A and 4B show one embodiment of an internal shaft of the bearing system of the present invention, wherein

FIGS. 6A and 6B show one embodiment of a static member of the bearing system according to the present invention, wherein

FIGS. 7A and 7B show an intracorporeal device within a vessel, wherein

DETAILED DESCRIPTION OF THE INVENTION

The present invention is bearing system for connecting an operating head and a catheter system in an intracorporeal device in which a rotatable drive shaft extends within a non-rotating outer catheter (also referred to as "catheter"). The bearing system includes a static member mountable to the distal end of the catheter. The mounting of the static member to the catheter is to be understood to include mounting of the static member directly to the catheter or indirectly, through mounting to any intermediary component that may be present between the static member and catheter. The bearing system further includes an interior shaft that is rotatably mountable to the drive shaft and the operating head. The mounting of the interior shaft to the drive shaft and/or operating head is to be understood to include mounting of the interior shaft directly to the drive shaft and operating head or indirectly to any intermediary component that may be present between the internal shaft and operating head and/or the internal shaft and drive shaft. At least one connecting structure retains the static member and internal shaft. The bearing system of the present invention provides limited tilting of the operating head with respect to the rotatable drive shaft and non-rotating catheter, thereby facilitating routing of the intracorporeal device through tortuous paths and improving operation of the device at the target site.

The static member has at least one opening through which at least a portion of the connecting structure rests against a seat of the interior shaft. The position of the connecting structure within the seat enables the bearing to accept a rotational load of the drive shaft rotating at a variety of speeds and/or thrust load in the direction of the longitudinal length of the catheter. The connecting structure may contact different portions of the seat as the interior shaft tilts relative to the catheter. For example, where the operating head is directed over a flexible guide wire through the body, the bearing system permits the operating head to tilt along with the guide wire. The operating head may also briefly contact an internal surface of the body and be deflected by tilting away from the internal surface. In this manner, the attached operating head may be flexible to orient to particular angles from the longitudinal axis of the catheter.

As used herein to describe various components of the intracorporeal device and bearing system, the term "proximal" refers to a direction or area away from the end of the device to be first inserted into a body cavity and closest to the external device controls, and "distal" refers to the direction or area toward such insertion portion, i.e. operating head, and farthest from the external device controls. The intracorporeal device is provided with components that are inserted and navigated within a patient's body while an operator uses the intracorporeal device, and these components are generally continuous with and/or in communication with components for placement external to the patient.

The intracorporeal device that may contain the bearing system of the present invention may be led through a pathway in the body of a human or animal. The device may be used within any body cavity having a sufficiently hollow space to accept the operating head of the device. Various types of body cavities may include a vascular cavity, a gastrointestinal cavity, an air exchange cavity, or the like. The body cavity may be a tubular-shaped structure, such as an artery, a vein, or another blood vessel, or another lumen structure, such as a ureter, a fallopian tube, a nasal passageway, and other tubular tissues in a body. For example, the system may be used for saphenous vein graft interventions or interventions with coronary (and other) arteries. The body cavity may also be an organ, such as kidney, gall bladder, lung, or the like. Further, the body cavity may form a part of another system, such as a lymph node, spinal canal, or the like.

The intracorporeal device incorporating the bearing system of the present invention may be implemented for treatment or diagnosis in a variety of surgical operations and procedures, such as translumenal microsurgery. For example, the system may be used in the treatment of blood vessel conditions, such as removal of accumulations of materials in coronary blood vessels and in blood vessels remote from the heart. Other applications include, and are not limited to, the treatment or diagnosis of benign prostate hyperplasia; gynecological conditions involving accumulation of material in fallopian tubes and elsewhere, such as fibrotic disease; urological conditions, such as kidney stones; the treatment of gallbladder conditions, such as gall stones; and spinal cord and dural tube conditions, such as stenoses of the spinal canal. Medical fields of use include cardiology, radiology, urology, neurology, etc.

A wide variety of operating heads for diagnostic or therapeutic surgical procedures within a body cavity that receives rotational torque from a drive shaft is well known to those skilled in the art. For example, types of operating head may include a cutting head having one or more cutting surfaces, such as a rotary cutter with one or more blades or abrasives; a heating element for performing thermal ablation; electrodes for performing electrosurgical cutting and cauterization; abrasive elements for performing mechanical ablation; fluid jet stream tip; optical waveguides for performing laser ablation; ultrasonic transducers for imaging and ablation; angioscopic imaging devices; and the like.

One example of an intracorporeal device useful in diagnosis may include a probing operating head, such as an ultrasonic transducer. The diagnostic device may be useful in several medical fields. For example, in cardiology the operating head may be used to inspect the inside of the heart to identify abnormal structures or functions. The device may also be useful in measuring blood flow through the heart and other vessels. In urology, the device may be used to see kidney stones, measure blood flow through the kidney, detecting prostate cancer, etc.

In some particular applications of such an intracorporeal device, undesirable matter must be removed by maneuvering the intracorporeal device within the body cavity. If not removed, the matter may inhibit or cut off the flow of fluid, such as blood, and other essential components through the body cavity. For example, atherosclerosis is a condition arising from the deposition of fat-like matter, i.e. plaque, on the walls of blood vessels. As a result of accumulated obstructions, blood flow becomes restricted or blocked, creating health risks, including coronary artery disease, angina and heart attacks. The operating head for matter removal typically has one or more cutting surfaces, such as blades and/or abrasive coated burrs, which contact and ablate the matter. The drive shaft usually conveys high speed rotation, e.g. about 500 to 200,000 rpm's, such as about 40,000 rpm's, to the operating head to cause the cutting surfaces to ablate the matter. The intracorporeal matter removed by the present invention may be any unwanted material contained within a body cavity, such as artherosclerotic disease, calcified plaque, thrombus, a gallstone, and other debris, a body part such as a valve or portion thereof.

Figure 1:
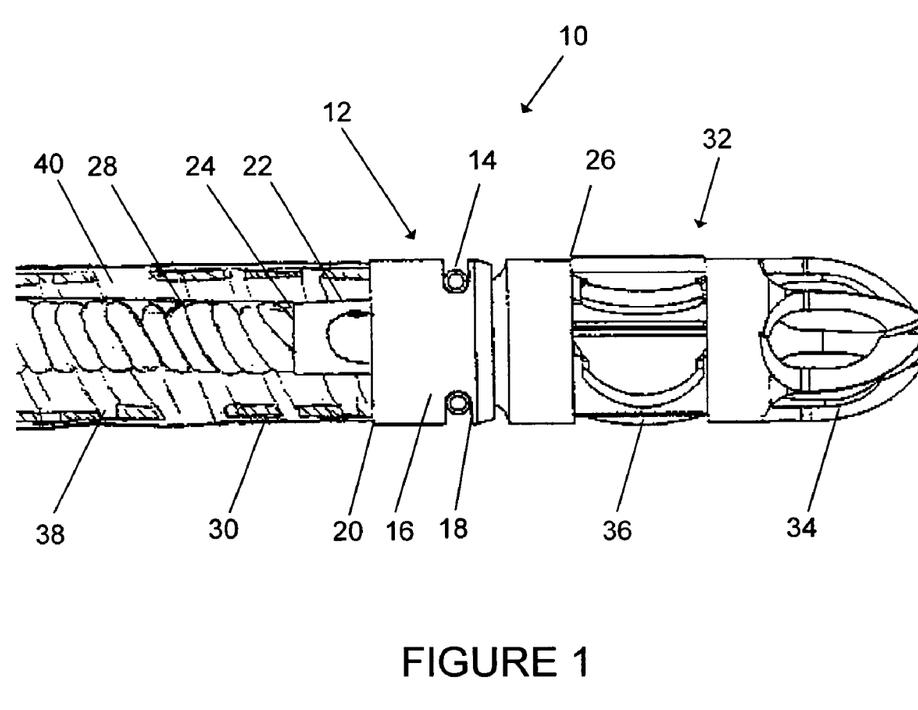
FIG. 1 shows an embodiment of the bearing system of the present invention connecting components of one type of intracorporeal device having a cutter operating head.

FIG. 1 shows one exemplary embodiment of an intracorporeal device 10 for removal of intracorporeal matter, having one example of the bearing system 12 of the present invention. The bearing system 12 comprises at least one connecting structure 14 and at least a contact portion of each connecting structure rests in an opening 18 of a static member 16. The contact portion 54 of the connecting structure extends through the opening to engage an internal shaft 22 located beneath the static member.

The internal shaft serves as a stable connector between the drive shaft and operating head to permit rotational torque to be translated from the drive shaft to the operating head. The internal shaft 22 is in rotatable communication, i.e. mountable, with a drive shaft 28, including any intermediary component, typically at a fixed junction between the distal end of the drive shaft and the proximal end 24 of the internal shaft. For example, the proximal end of the internal shaft may be welded or otherwise firmly attached to the drive shaft, or intermediary component. The internal shaft is also in rotatable communication, i.e. mountable, with an operating head 32 including any intermediary component, often times at a fixed junction with the distal end 26 of the internal shaft. The drive shaft 28 is rotatable and translatable within an outer catheter 30 of a catheter system 38, whereas the outer catheter does not rotate along with the rotation of the drive shaft.

In operation, the operating head is rotated as the internal shaft and drive shaft rotate. In one embodiment of intracorporeal device, the operating head 32 may include at least one cutter, for example, a dual cutter system having a distal cutter 34 and a proximal cutter 36. Further details of a cutter removal device suitable for use in connection with the bearing system of the present invention, are disclosed and described in U.S. Pat. No. 6,565,588 B1, filed on Nov. 28, 2000, the contents of which is incorporated herein by reference.

The static member 16 is fixedly coupled, e.g. bonded by welding and/or applying adhesives, i.e. mountable, to the distal end of the outer catheter 30, or to any intermediary component attached to the distal end of the outer catheter at a fixed junction typically with the proximal static member end 20. Between the inner surface of the outer catheter and the outer surface of the drive shaft may be a catheter conduit 40 extending down the length of the catheter system.

Figure 2:
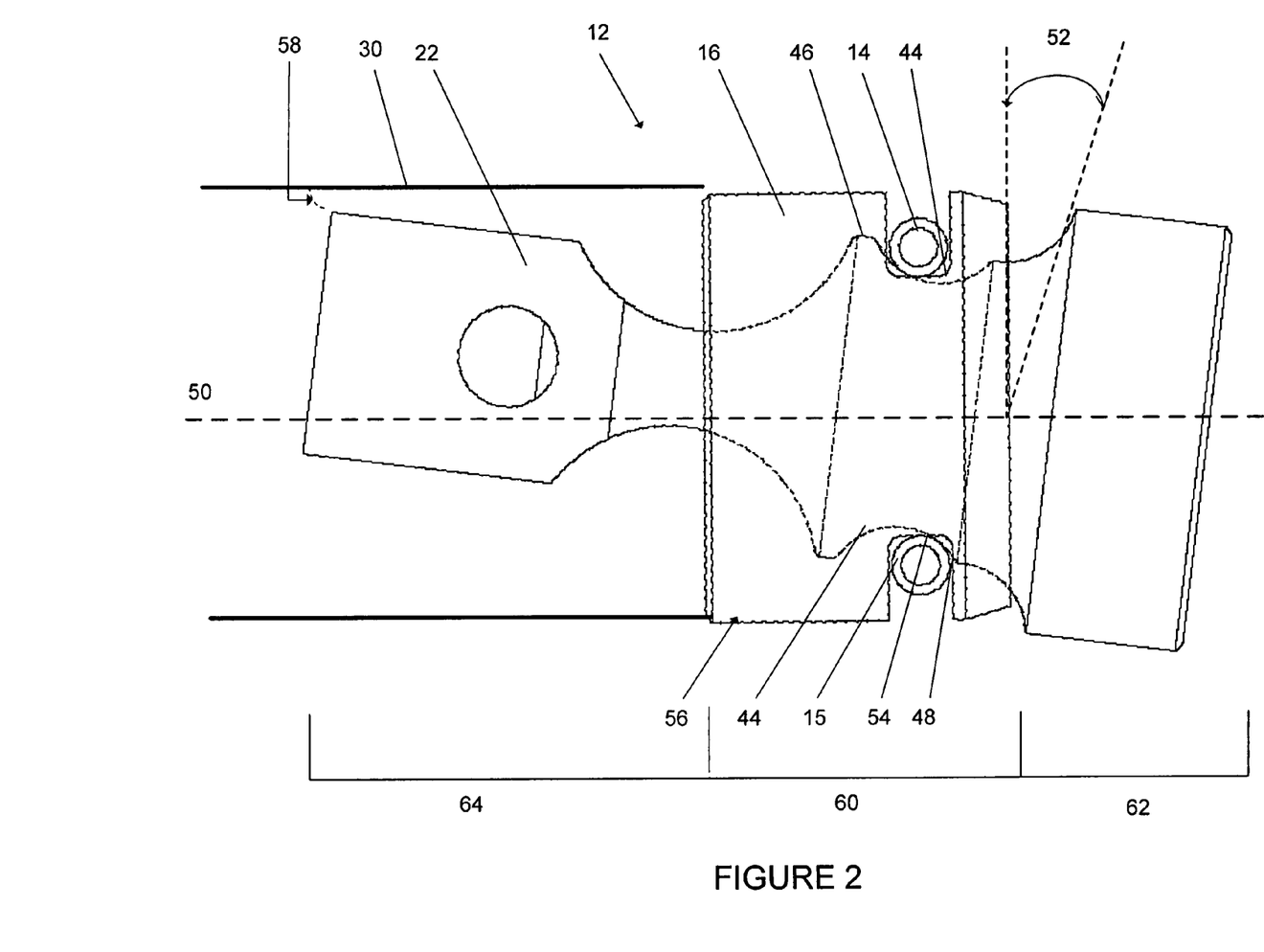
FIG. 2 shows a side view of the bearing system of the operating head, illustrating a superimposed view of the static member enclosing a portion of the internal shaft and two connecting structures engaging the static member and internal shaft, according to the present invention.

As shown in FIG. 2, one embodiment of bearing system 12 includes an enclosed portion 60 of the internal shaft 22 extending through the static member 16 and an exposed portion 62 of the internal shaft that is not surrounded by the static member. The inner diameter 56 of the static member 16 is larger than the enclosed portion 60 of the internal shaft 22. In some embodiments, the internal shaft may further include a back portion 64 that extends proximal from the enclosed portion 60 and into the distal end of the catheter 30.

One or more connecting structures, and often two opposing connecting structures 14, 15, are coupled to the static member 16 and engage the enclosed portion 60 of internal shaft 22 at one or more coupling points. The contact portion 54 of the connecting structure that extends through the static member opening is maintained within the seat 44 to resist springing of the drive shaft away from the catheter, especially where strong axial forces are present during operation, such as where a cutting operating head contacts dense matter.

The connecting structure may be any geometry including a contact portion that may extend through the opening and rest in the seat. For example, the connecting structure may be a rod, ball, ring or other structure. In one instance, the connecting structure is a rod comprising a cylindrical wire and may be any convenient length, such as about 0.05 to 0.20 cm. The length of the connecting structure depends, intra alia, on the amount of load that the bearing system is required to handle. In one embodiment, the contact portion of the connecting structure that sits within the seat defines a line of contact with the seat, rather than a point of contact, in order to distribute the load exerted on the intracorporeal device over a larger area.

The coupling point of the connecting structure to the static member may be at various point(s) on the connecting structure other than at the contact portion of the structure. For example, where the connecting structure is a rod, the opposing ends of the rod may be attached to the static member. The coupling technique is often welding, but may also be other means such as adhesives, snap-in mechanisms, etc. The choice of coupling means is sufficient to retain the connecting structure onto the static member while the device is subject to various forces of operation. Welding may produce a very small affected zone and maintain the hardness properties of the connecting structures at the contact point with the inner shaft.

Oftentimes, the connecting structure is constructed from a hard material with a high tensile strength, such as 350,000 to 400,000 psi. For example, the connecting structure may be stainless steel that has undergone a cold drawing process or heat treatment, as such processes are known in the art. In one embodiment, the connecting structure may be "high ten wire" (304 v) (for example, round wire by Fort Wayne Metals, located in Fort Wayne, Ind.). The cold drawn steel connecting structure is found to have a greater tensile strength than typical machine treated steel. The diameter of the connecting structure may be any size that permits the connecting structure to conveniently extend to contact the seat. For example, the connecting structure may be a rod having an outer diameter of 0.005 inch to 0.020 inch and more typically 0.010 inch.

The internal shaft 22 is a rigid structure capable conveying rotational torque from the drive shaft to the operating head. The internal shaft includes the seat 44 on its outer surface and defines the area in which the connecting structure may contact.

Each seat may be a concave base for accepting one connecting structure. The seat is typically one continuous surface that circumscribes the perimeter of a portion of the internal shaft. The seat has a length from the back 46 of the seat, which may be a first ledge, to the front 48 of the seat, which may be a second ledge. The seat may have a width and a curvature sufficient to accommodate the flexibility of the operating head and to retain the connecting structure during high thrust loads.

Usually, the connecting structure and seat are made of different materials and have different hardness in order to discourage deterioration of the contact surfaces during an operation. For example, the connecting structure 50 may be made of material that is softer than the material of the seat 44 of the internal shaft 22. In one embodiment, the connecting structure may be made of cold drawn steel and the seat may include a harder material, such as a titanium nitride coating. In another embodiment, the seat may be made of cold drawn steel and the connecting structure may include a harder material, such as a titanium nitride coating. The difference of hardness between the outer surfaces of the connecting structure and seat is sufficient to inhibit wear of the connecting structure and seat as the two surfaces rub against each other under the load of operation. For some operations, such as high rotational cutting of intracorporeal matter by the device, the length of life of the connecting structure and seat surfaces need not be very long, e.g. about 10 minutes at 40,000 RPM. However, high durability is required even for this short time period because the operating head may need to rotate millions of times during a cutting operation.

Where the internal shaft tilts toward certain directions with respect to the static member, which is in fixed relation to the catheter, the connecting structure may contact a new point on the seat to adapt to the tilting of the internal shaft. For example, where the bearing system includes two connecting structures and the angle of tilt of the internal shaft is toward the direction of the second connecting structure 14, e.g. angle in a downward direction as shown in FIG. 2, the first connecting structure 14 may become positioned toward the back 46 of the seat 44 and the second connecting structure 15 may become positioned toward the front 48 of the seat 44. Where the angle of tilt is in the opposite direction, e.g. upward, the vice versa may occur. In this case, the first connecting structure 14 may reposition toward the front of the seat 44 and the second connecting structure 15 may reposition toward to the back of the seat. In embodiments that include a continuous seat that circumscribes the perimeter of the internal shaft, the operating head may have the ability to tilt in any direction of 360 degrees about the catheter.

The tilt of the internal shaft is further permitted by a clearance gap 58 between the outer diameter of the internal shaft and the inner diameter of the surrounding device component, such as the catheter 30, static member 18 or other intermediary component, which immediately encloses the internal shaft's proximal portion, e.g. back portion 64 and/or enclosed portion 60. In some embodiments, the clearance gap is in a catheter conduit. The proximal end of the internal shaft usually does not tilt enough to contact the inner catheter surface. Typically, the internal shaft may tilt within the space provided by the clearance gap in any direction about the connecting structure. The articulation of the operating head may be within any axis of a cone-shape lying along the longitudinal axis of the catheter, i.e. the operating head may sweep within a full 360 degree direction from the longitudinal axis of the catheter. In this manner, the internal shaft may orient the operating head at an angle 52 about the longitudinal axis 50 of the catheter.

An angle limit may be designated as the maximum amount of flexibility of the operating head. The angle limit may be any convenient amount of tilt for the operating head. For example, the angle limit may be between about 10 to 20 degrees, often about 10 degrees. Thus, the amount of possible flexibility of the operating head is from greater than zero degree to the angle limit, where zero degree is where the operating head is positioned along the same longitudinal axis as the catheter.

Figure 3A:
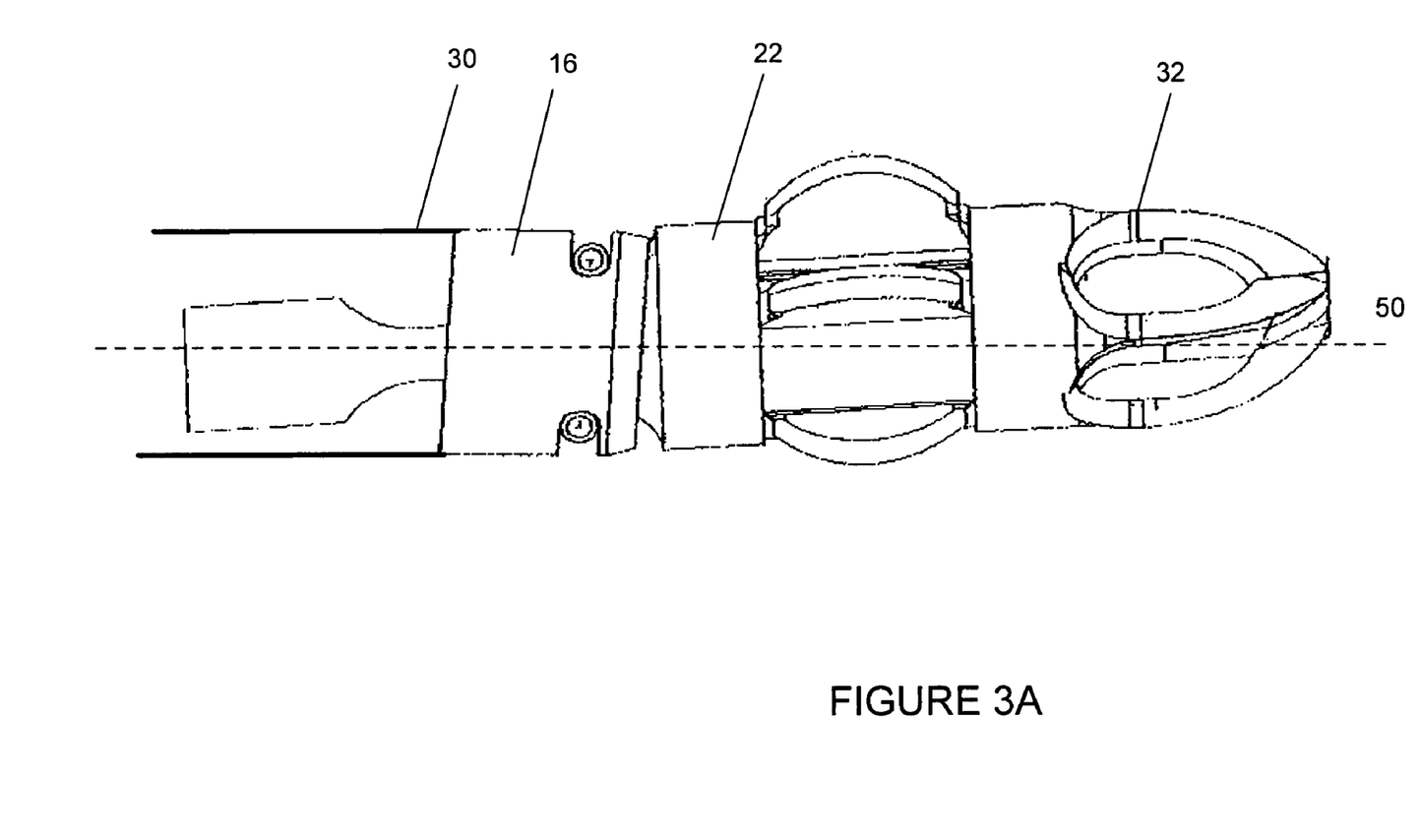
FIG. 3A shows the bearing system with the interior shaft in a tilted orientation relative to the static member and FIG. 3B shows the bearing system in a non-tilted position.

FIG. 3A shows the internal shaft 22 and the operating head 32 in a tilted position with respect to a longitudinal axis 50 defined by the catheter. During the operation of the intracorporeal device, the internal shaft 22 attached to the drive shaft (not shown) and the operating head 32 may be tilted as a unit relative to the static member 16. The static member and outer catheter 30 may remain fixed or static relative to the rotation of the drive shaft and the operating head.

Figure 3B:
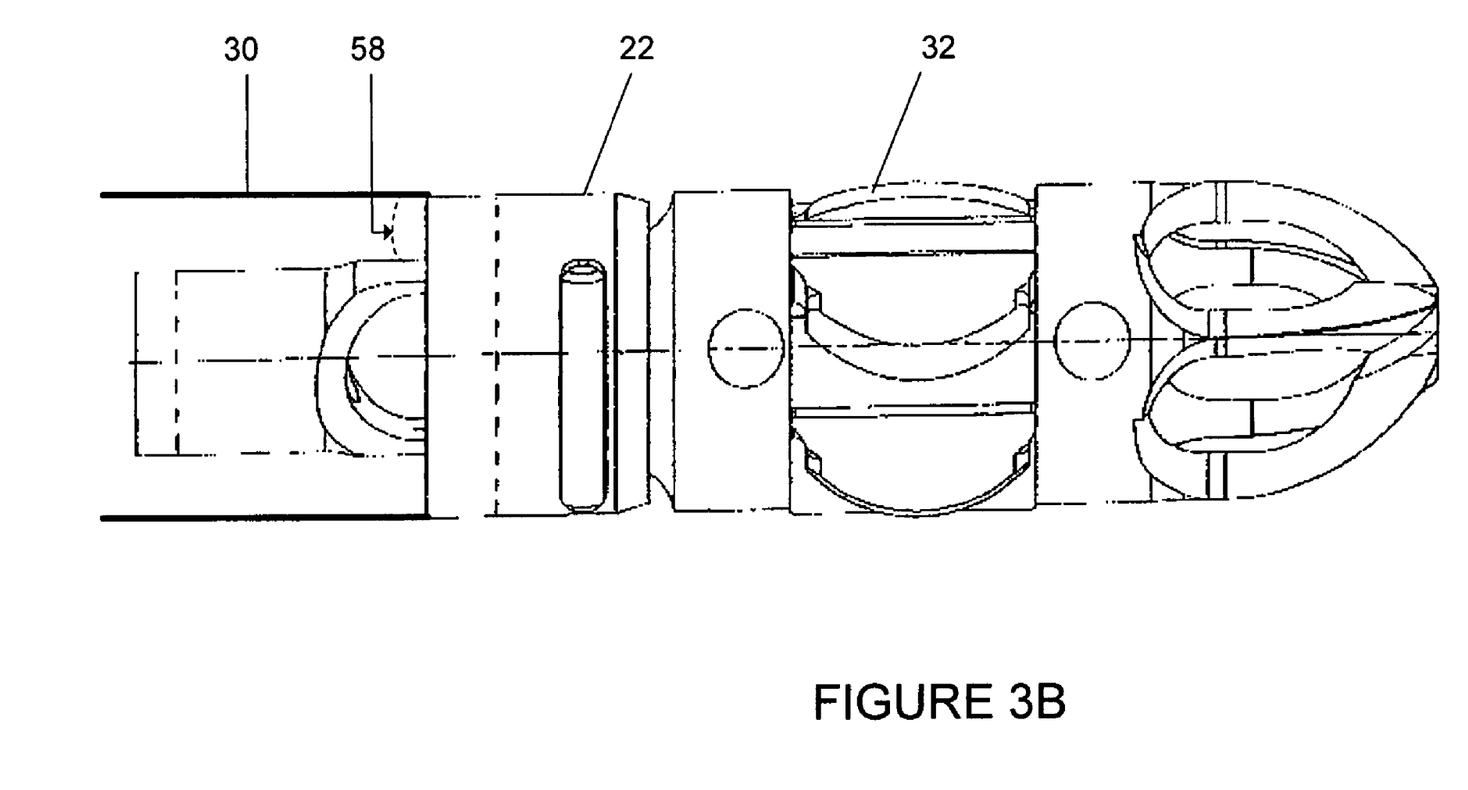

FIG. 3B shows the internal shaft 22 and the operating head 32 in a non-tilted position. The operating head is aligned along the same axis in which the catheter is positioned. The total height of the clearance gap 58, such as between the internal shaft and the inner surface of the catheter 30, is determined as the internal shaft extends along the same axis as the catheter. The height of the clearance gap in any direction from the internal shaft extending radially outward is typically selected to provide optimum tilting capability of the operating head to determine the permissible amount of tilt. For example, the clearance gap may be about 0.001 inch to 0.005 inch.

Figure 4A:
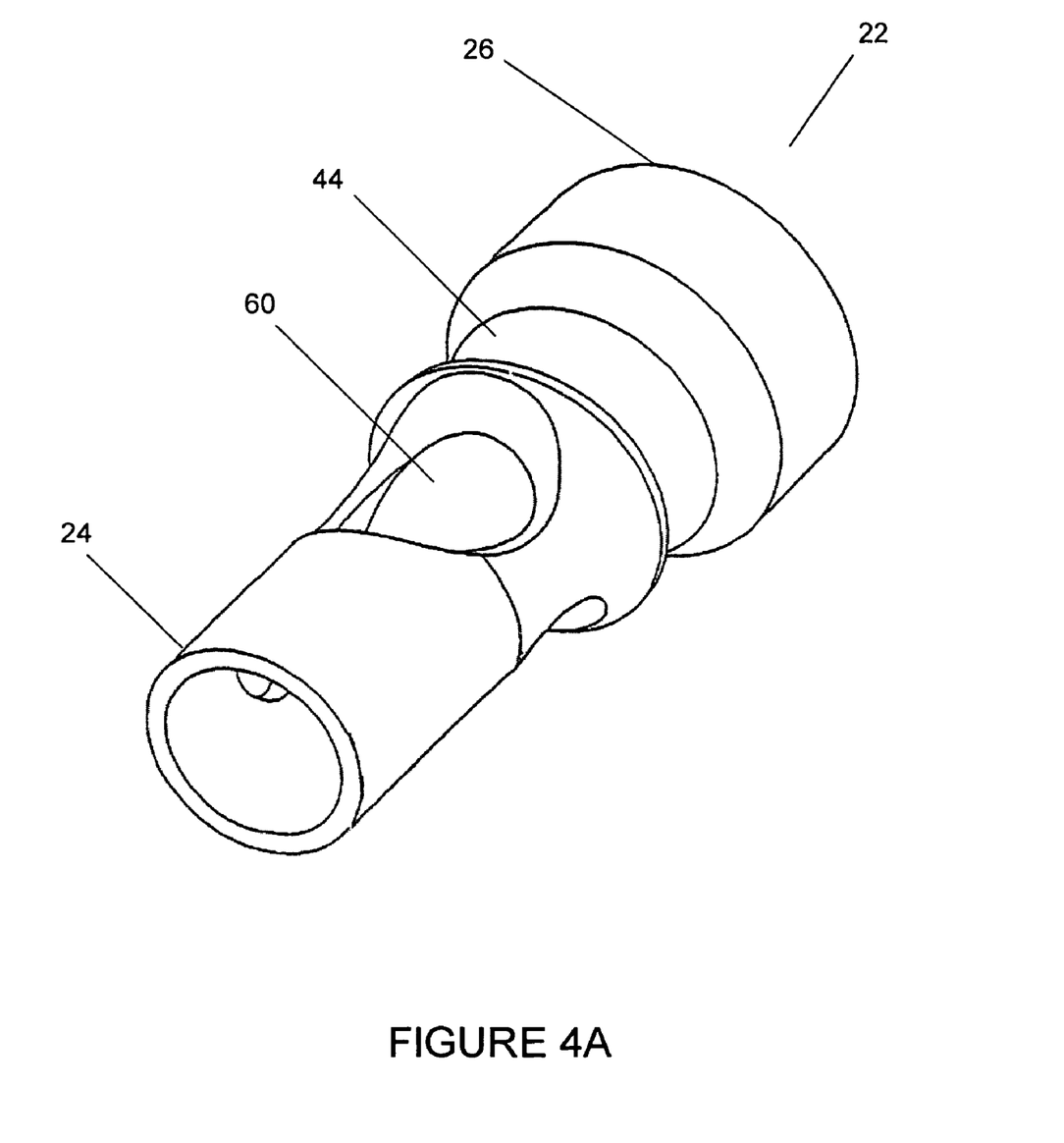
FIG. 4A shows a schematic view of the internal shaft and FIG. 4B shows a side profile of the internal shaft.
Figure 4B:
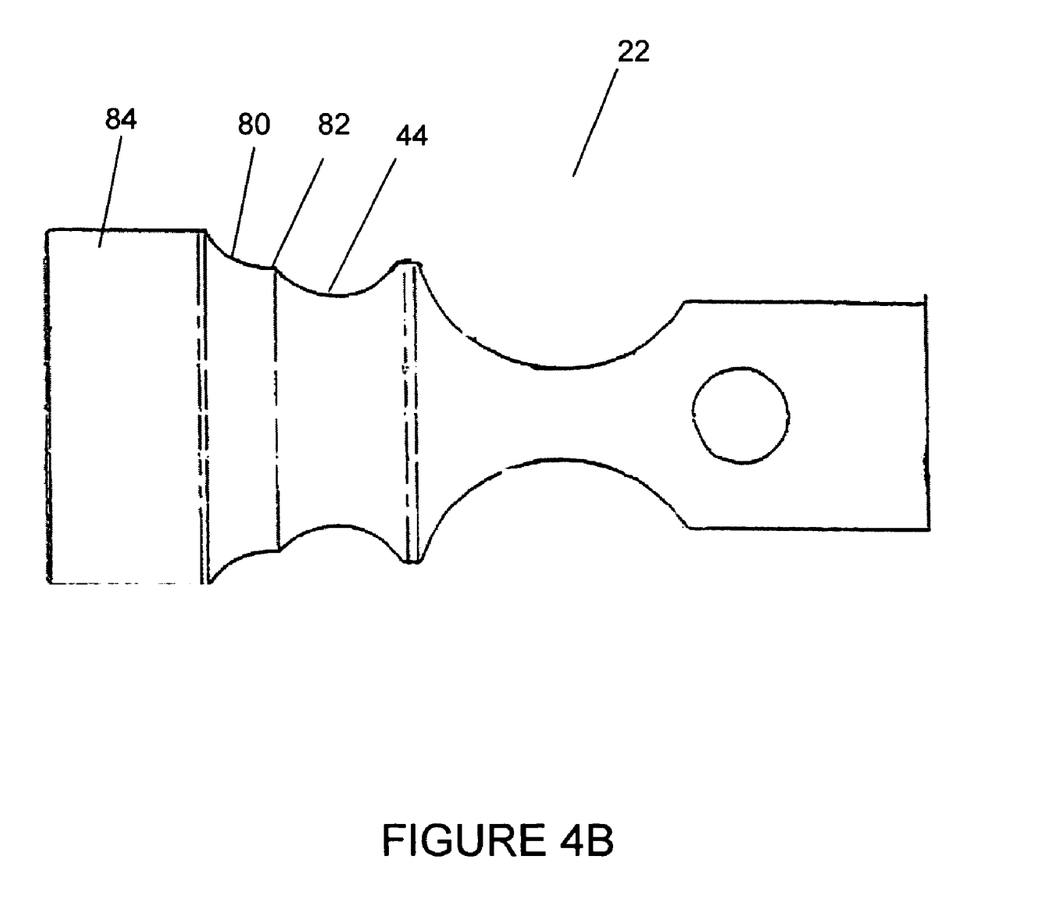

Some embodiments of the internal shaft component of the bearing system are shown in FIGS. 4A and 4B. The internal shaft 22 may be provided with at least one port 60 that serves as an opening for fluids and/or particles to travel between catheter conduit 40 (shown in FIG. 1) and the operating head. The port is typically located in an area of the internal shaft that is proximal from the seat 44. At least a portion of the internal shaft port 60 may not be covered by the static member. The port may be any convenient shape, such as oval.

Often during a procedure, it is required for fluid, particles or tools to travel or extend through the intracorporeal device to or from the target site. The components of the intracorporeal device must not prevent such passage. For example, the flexibility of the operating head must not block passage through the device.

Figure 5:
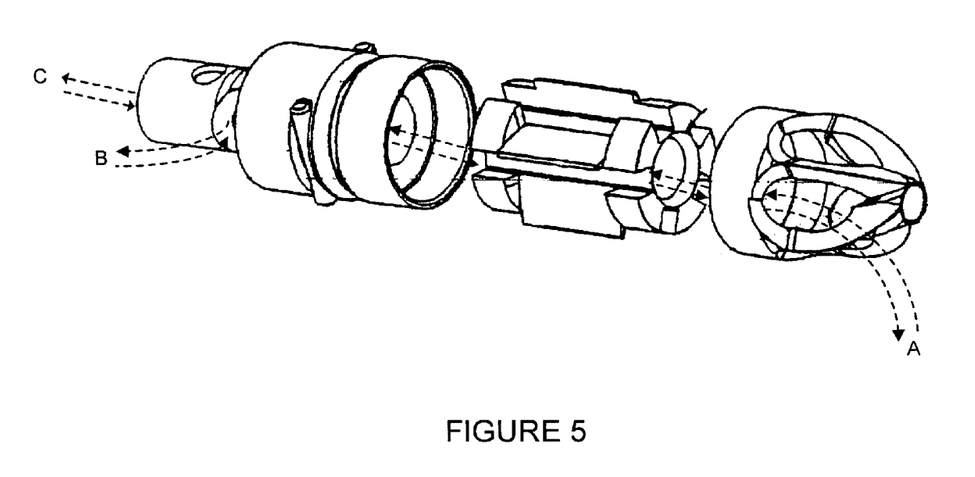
FIG. 5 shows one embodiment of a bearing system of the present invention and unassembled parts of one type of cutter operating head.

As shown in FIG. 5 by the distal end of one unassembled intracorporeal device, the internal shaft 22 may include a lumen 62 to permit flow of fluid or particles between the operating head and catheter system or to accommodate tools, such as a guide wire. Since the lumen extends within the internal shaft, the passageway is not cut off by the tilting of the internal shaft within the clearance gap or by the engaging of the connecting structures with the static member and internal shaft. Typically, the lumen extends from the operating head to the catheter or the drive shaft. The lumen may be continuous with an internal cavity 64 or conduit in the operating head, such as extending through a distal cutter 66 and proximal cutter 68. The passageway may further continue to one or more operating head port 70 that opens to the exterior of the operating head, e.g. to the body cavity. Furthermore, the passageway may continue in a proximal direction from the lumen of the internal shaft through a conduit in the drive shaft and/or through the port 70 to the catheter conduit 40 (shown in FIG. 1).

In a direction from B to A, for example, the passageway may be used for aspiration, therapeutic compounds, saline and/or blood, etc. flowing from the proximal end of the catheter through the port to the internal shaft lumen, to the operating head internal cavity and travel out of the operating head port. In addition, the passageway may lead from a conduit in the drive shaft to the internal shaft lumen, and to the operating head internal cavity and travel out of the operating head port in a direction C to A, or through the most proximal tip of the operating head, such as the passageway for a guide wire. Furthermore, in a direction of the passageway from A to B, for example, particulates that have been cut from a body cavity, blood, or other substances may be removed from the body by traveling through an operating head port and internal cavity to the internal shaft lumen, and through the internal shaft port to the catheter conduit. The distal end of the internal shaft may be sealed to the operating head to provide a continuous and sealed passageway.

The outer diameter of distal end 26 of the internal shaft any convenient diameter, e.g. about 1 mm to 3 mm, and more typically about 1.75 mm. A cap 84 portion of the internal shaft may be located at the distal end of the internal shaft. In one embodiment, the diameter of the cap 84 has about the same or larger diameter as the static member 16. The cap 84 may also provide a partial cover for the operating head. During assembly of the bearing system, since the circumference of the cap is larger than the circumference of the stop of the static member, when the static member is being placed onto the operating head, the static member comes to a contact surface when its stop reaches the proximal cap and is therefore prevented from sliding through the proximal cap towards the operating head. The diameter of the proximal end 24 of the internal shaft is typically the same diameter as the connecting portion of the drive shaft, or any intermediate component between the internal shaft and drive shaft. For example, the proximal internal shaft end's outer diameter may be about 0.03 inch to 0.05 inch, and more typically 0.24 inch.

As shown in FIG. 4B, the internal shaft may also include a contact surface 80, which may contact the static member when the internal shaft tilts to the designated angle limit. In some embodiments, the contact surface 66 may be a groove, wall, etc. that extends continuously around the diameter of a portion of the internal shaft. In one embodiment, the contact surface is concave in shape and is downward sloping from its distal to proximal end. The first ledge 82 may separate the contact surface 80 from the seat 44.

Figure 6A:
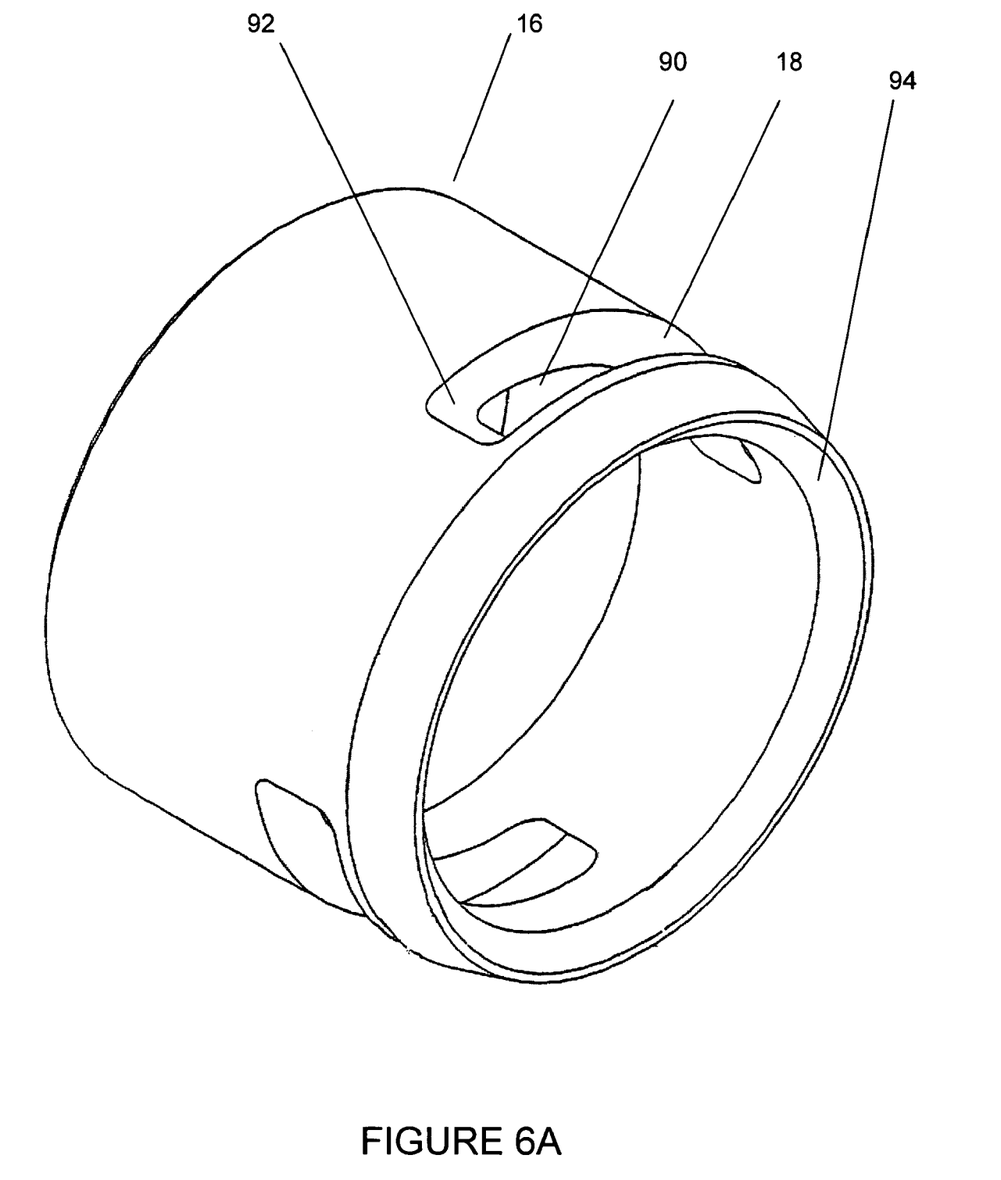
FIG. 6A shows a distal to proximal schematic view of the static member.
Figure 6B:
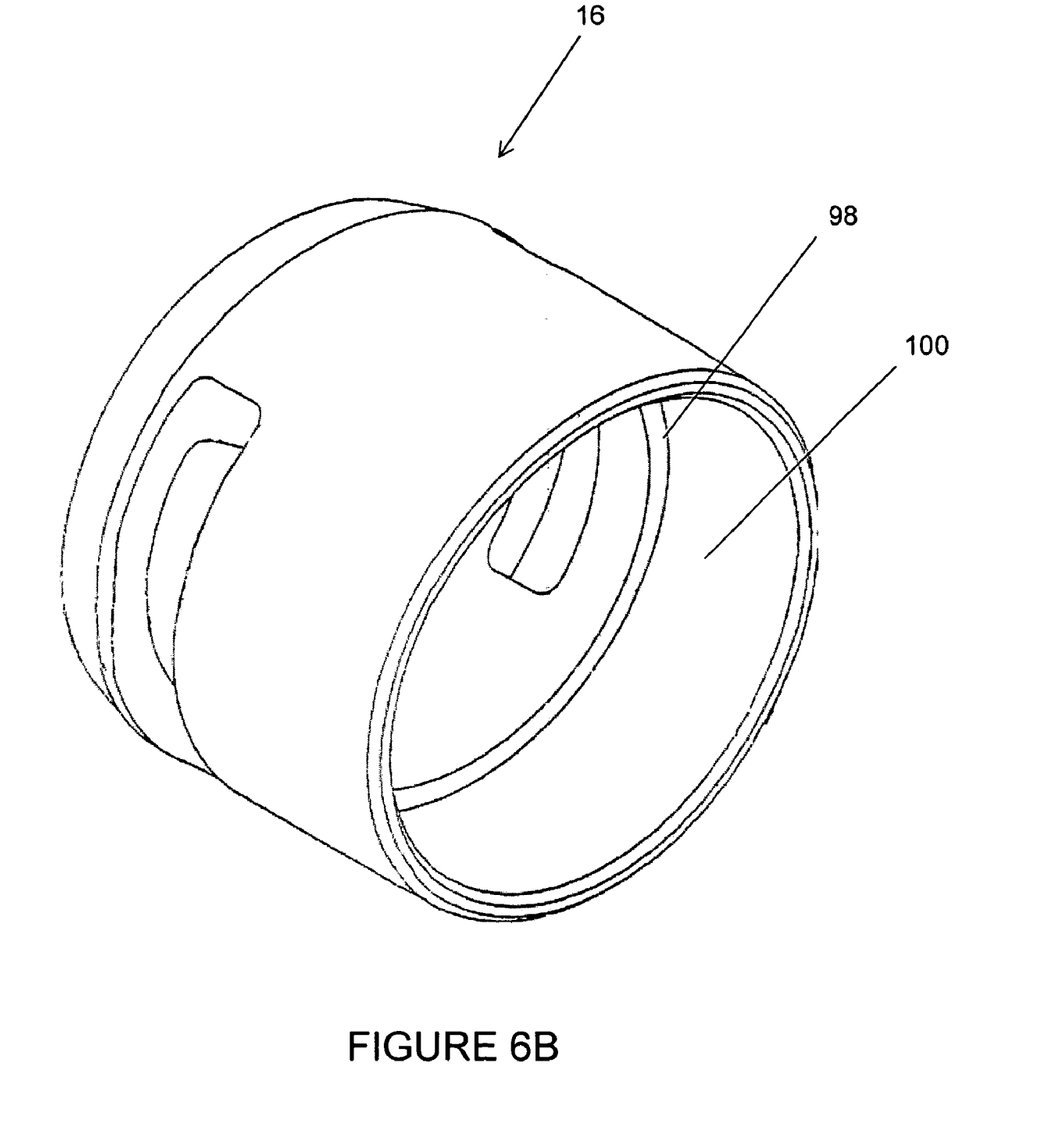
FIG. 6B shows a proximal to distal schematic view of the static member.

As shown in FIGS. 6A and 6B, the static member 16 is an outer sleeve that surrounds at least an enclosed portion of the internal shaft and is stationary relative to the rotating internal shaft. The static member may be any convenient shape and usually a cylindrical shape. Typically, the static member is an annular sleeve, i.e., generally cylindrical and hollow, and has an inner diameter that is greater, usually slightly larger, than the outer diameter of the internal shaft enclosed portion.

The static member comprises at least one opening 18 that extends through the static member. The opening is sized and shaped to permit a length of the connecting structure, i.e.

contact portion, to rest through the opening and contact the seat, such as a linear slot. Where the opening is a linear slot, the slot may be traverse in a direction perpendicular to the longitudinal axis of the catheter. The number of openings usually equals the number of connecting structures in the bearing.

The opening may reside within an indentation 90, i.e. recess, on the static member. The indentation is typically shaped to snuggly hold the connecting structure and often has an internal width that is slightly larger than the connecting structure. Thus, the indentation may be a linear shape, similar to or the same as the shape of the connecting structure. In one embodiment, the indentation is shorter than the length of the connecting structure so that opposing connecting structure ends may extend past the indentation. The indentation 90 may have opposing raised ends 92 to receive the ends of the connecting structure preventing the connecting structure from being pushed entirely through the opening 18. In another embodiment, the length of the indentation may be the same as or greater than the length of the connecting structure such that the connecting structure comfortably sits within the indentation. The connecting structure is usually fixed, e.g. welded, at one or more points to the indentation.

The static member may further include a stop 94 to bear against the interior shaft, such as at the contact surface of the internal shaft, when the operating head is oriented at an angle limit along the longitudinal axis of the catheter. The stop 94 may be, for example, a chamfered wall, which contacts the contact surface of the internal shaft and the angle of the wall may further encourage the tilt of the internal shaft. In some embodiments, the material comprising the stop is sacrificial and some wear during operation may occur as the internal shaft contacts the stop during rotation. However, wear of these components is not so great as to compromise the operation. In other embodiments, the stop and the contact surface may comprise materials of varying hardness, as described above with regard to the connecting structure and seat.

The bearing system may also include one or more fittings to assist in connecting components of the intracorporeal device. As shown in FIG. 6B, the inner surface 100 at a proximal portion of the static member 16 may be provided with a ridge 98. The ridge 98 may be any length and height that is sufficient to serve as a fitting for the distal end of the catheter. In some embodiments, the ridge is one continuous raised edge that encircles the inner diameter of a proximal portion of the static member. The ridge may catch the catheter slid into the static member. The ridge may also provide a locator surface bonding the catheter to the static member.

In order to conveniently fit within a small body cavity and other confined space in the body, the bearing system is typically very small, e.g. micron dimensions. For example, the bearing length may be about 1.00-2.00 mm and more often about 1.50-1.60 mm. Furthermore, the use of the small bearing system may permit various operating head components to be shorter. Thus, the overall length of the operating head may be reduced compared to devices having a fixed junction between the catheter/drive shaft and the operating head. For example, the amount of length reduction may be between 0.5 mm to 1.0 mm and more often about 0.8 mm.

Figure 7A:
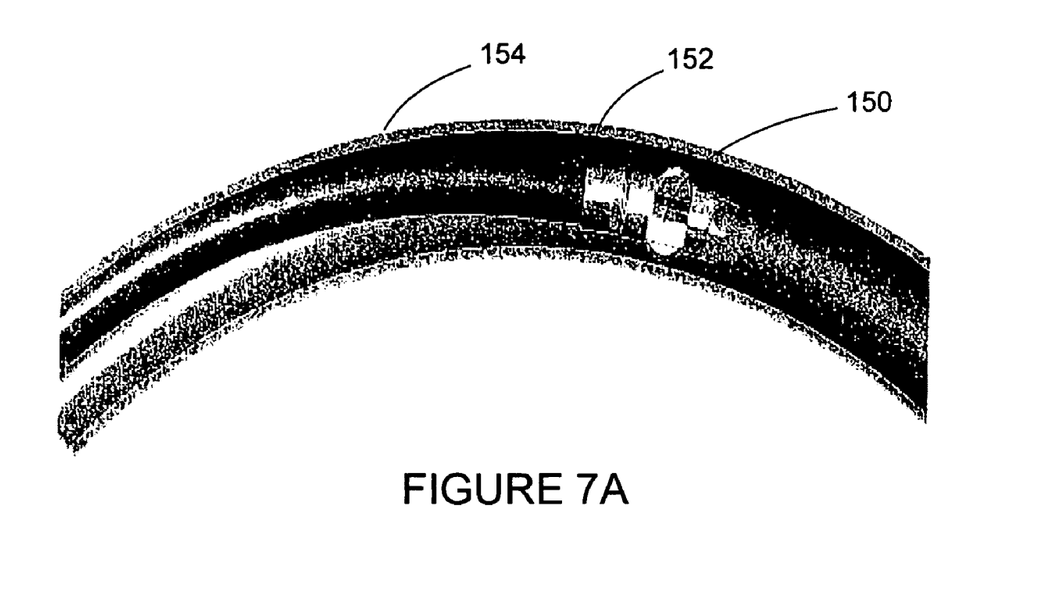
FIG. 7A shows a tilted intracorporeal device having one embodiment of bearing system of the present invention.
Figure 7B:
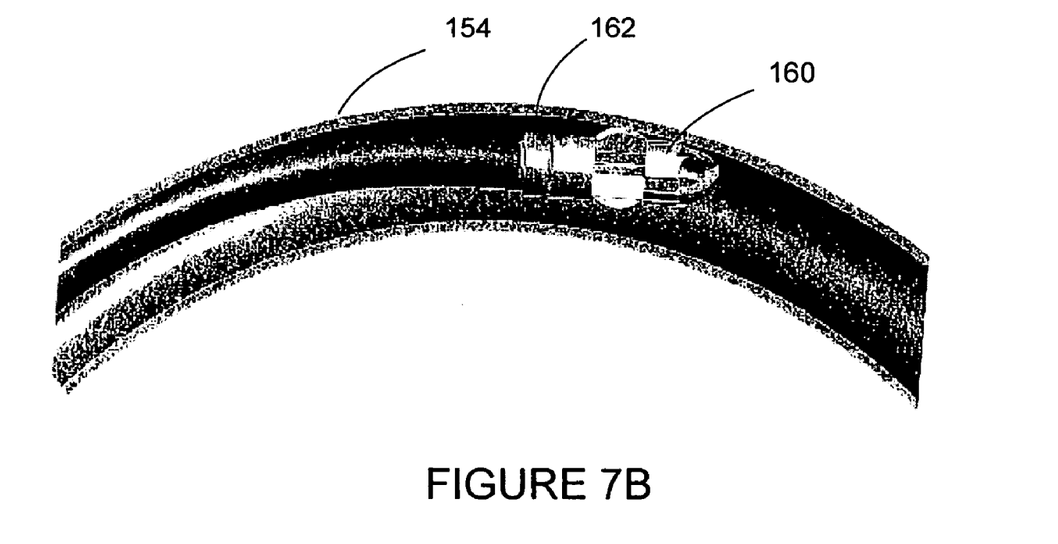
FIG. 7B shows non-tilted intracorporeal device contacting the vessel wall.

During operation of the present bearing system, the device is directed through a curve in a body, and the drive shaft, internal shaft and operating head tilt relative to the outer catheter. FIG. 7A shows a flexible intracorporeal device 150 having a bearing system 152 according to the present invention, guided through a body cavity 154, such as a vessel. The operating head avoids excessive rubbing against the wall of the cavity or lumen, because the operating head is deflected as it contacts the wall. By comparison, FIG. 7B shows a prior art intracorporeal device 160 having a non-flexible junction 162 between the operating head and catheter, guided through the curve in the body cavity 154. Where the operating head is not free to orient at an angle, the operating head may scrape along the length of the curved portion of the wall and thus damage the wall.

Figure 8:
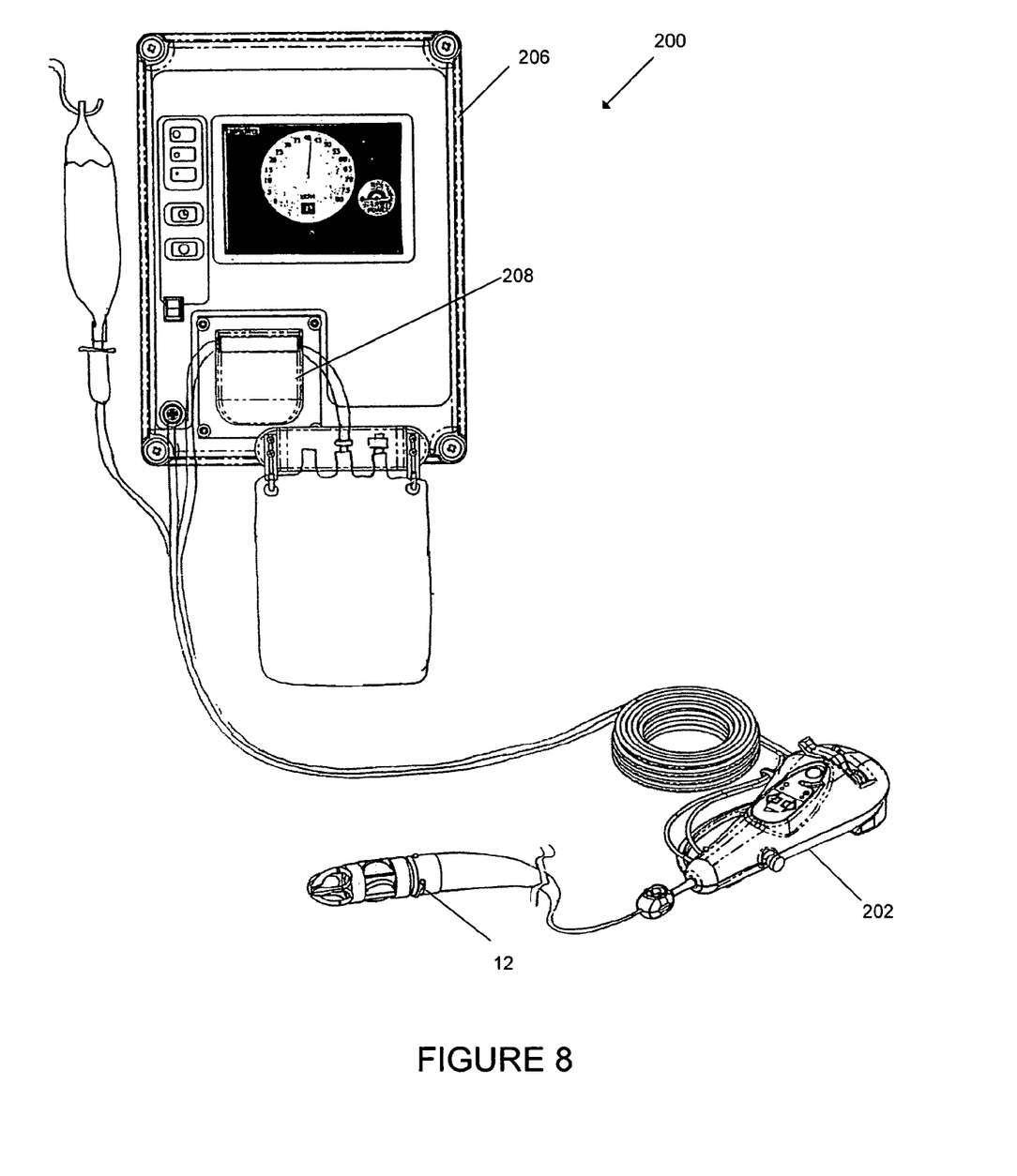
FIG. 8 shows an intracorporeal device having a control system and drive system.

Typically, in order to rotate the drive shaft, a drive system e.g. a high-speed electric motor, or a pneumatic-powered motor, is included. Oftentimes, the drive shaft may be rotated at high speed of about 500 rpm to 200,000 rpm may be used, more typically about 10,000 to 100,000 rpm and more often about 40,000 rpm, or more. In addition, one or more control systems may be included to direct the speed of rotation and to assist in the operation of the intracorporeal device. FIG. 8 shows one example of an intracorporeal device 200 having a bearing system 12 and a drive system housed within a tracking pod 202. This drive system and tracking pod are described in more detail in U.S. Provisional Patent Application No. 60/453,846.

A consol unit 204 may also be provided to direct control of the operating head 206. The consol unit may include adjustable controls that permit the operator to control operating parameters of the intracorporeal device. Controls may include a torque control to adjust cutter head rotational speed, a power control, a timer control to provide the length of time of the operation, a motor only control to turn on and/or off the motor without a pump 208, an aspiration only control to turn on and/or off the pump without the motor, and/or other convenient controls. Some of the controls and/or feedback data may be automatically triggered by software programs running in the console unit. Other controls may be directed by the operator activating controls on a control panel or display screen. For example, the display may have a touch pad in which the operator may touch control buttons and direct the removal system. The console unit may also be coupled to a variety of input devices for the operator to enter commands, such as a keyboard, personal data assistant, telephone, wireless communications devices, mouse, etc. Other communication features that are known or will be known in the future, for the operator to communicate with the console unit, either locally on the console unit or remotely, may be employed. Further details of such an intracorporeal device may be found in U.S. Provisional Patent Application No. 60/453,846.

The operating head may be smoothly rotated by the drive shaft, internal shaft and operating head rotating as an integral unit. As the internal shaft rotates, the connecting structure usually contacts against the seat of internal shaft of the bearing system. The distal end of the drive shaft and the operating head may be tilted as a unit relative to the static member and the catheter about the longitudinal axis of the catheter, which results in the operating head orienting at an angle. The static member may remain fixed relative to the rotation of the drive shaft and the operating head.

The present invention has been described above in varied detail by reference to particular embodiments and figures. However, these specifics should not be construed as limitations on the scope of the invention, but merely as illustrations of some of the present embodiments. It is to be further understood that other modifications or substitutions may be made to the described the bearing system that includes an internal shaft, static member and connecting structure, and the intracorporeal device, as well as methods of their use without departing from the broad scope of the invention. For example, the bearing system may include various shapes and sizes of the internal shaft, static member and connecting structure(s) in addition to those depicted and described.

We claim:

1. An intracorporeal device comprising:
   a catheter;
   a drive shaft that is rotatable within the catheter;
   an operating head that is rotatable about a longitudinal axis of the catheter; and
   a bearing system providing limited tilting of the operating head about the longitudinal axis relative to the catheter, the bearing system comprising:
      an internal shaft mounted to the drive shaft at a proximal end of the internal shaft and mounted to the operating head at a distal end of the internal shaft, the internal shaft including a seat;
      a static member mounted to a distal end of the catheter and in fixed relationship with the catheter; and
      a first and a second connecting rod, wherein a contact portion of each of the first and second connecting rods rests through a first opening and a second opening, respectively, of the static member and is received by the seat of the internal shaft,
      whereby, as the internal shaft tilts, the two connecting rods contact the seat of the internal shaft at various points and permit tilting of the operating head.

2. The intracorporeal device of claim 1, wherein the first and second connecting rods are made of a material having a different hardness than a material comprising the seat.

3. The intracorporeal device of claim 1, wherein the internal shaft further comprises a contact surface that restricts pivoting of the operating head beyond an angle limit.

4. The intracorporeal device of claim 3, wherein the static member further comprises a stop, at least a portion of the stop capable of meeting the contact surface when the operating head is oriented to the angle limit.

5. The intracorporeal device of claim 3, wherein the angle limit is about 5 to 20 degrees.

6. An intracorporeal device comprising:
   a catheter;
   a drive shaft that is rotatable within the catheter;
   an operating head that is rotatable about a longitudinal axis of the catheter; and
   a bearing system providing limited tilting of the operating head about the longitudinal axis relative to the catheter, the bearing system comprising:
      an internal shaft coupled to the drive shaft and coupled to the cutting head for rotation as a unit, the internal shaft including a seat;
      a static member mounted to a distal end of and in fixed relationship with the catheter and forming a unit that is in a stationary position during rotation of the drive shaft and the operating head, the static member having a first opening and a second opening; and
      a first connecting rod and a second connecting rod, the first and second connecting rods each having a contact portion resting through the first and second openings, respectively, of the static member and being received by the seat of the internal shaft,
      wherein the internal shaft is capable of orienting the cutting head about a longitudinal axis relative to the catheter and communicating rotational torque from the drive shaft to the cutting head, and whereby as the internal shaft tilts, the two connecting rods contact the seat of the internal shaft at various points and permit tilting of the operating head.

7. An intracorporeal device comprising: a catheter; a drive shaft that is rotatable with respect to the catheter; an operating head mounted for rotation with the drive shaft and that is rotatable about a longitudinal axis of the catheter; and a bearing system providing limited tilting of the operating head about the longitudinal axis relative to the catheter, the bearing system comprising a static member mounted to a distal end of the catheter and in fixed relationship with the catheter, an internal shaft mounted for rotation with the drive shaft and the operating head and at least partially extending through the static member, and a first connecting rod and a second connecting rod, the first and second connecting rods being received in a first slot and a second slot, respectively, provided in the static member and engaging a portion of the internal shaft, whereby as the internal shaft tilts, the first and second connecting rods contact a seat of the internal shaft at various points and permit tilting of the operating head.

8. The intracorporeal device of any of claims 1, 6 or 7, wherein the internal shaft further comprises a lumen to permit passage of fluid.

9. The intracorporeal device of claim 8, wherein the internal shaft comprises at least one port in fluidic communication with the lumen.

10. The intracorporeal device of any of claims 1, 6 or 7, further comprising a drive system and a control system.

11. An intracorporeal device of any of claims 1, 6 and 7, wherein the operating head comprises at least one of the following structures: a diagnostic device; a cutting surface; a heating element; an electrode; an abrasive element; a fluid jet tip; an optical waveguide; an ultrasonic transducer; or an imaging device.

12. An intracorporeal device of any of claims 1, 6 and 7, wherein the internal shaft comprises a portion extending through the static member, an exposed portion that is distal to the static member, and a proximal portion that is proximal to the static member.

13. An intracorporeal device of any of claims 1, 6 or 7, wherein the internal shaft seat defines a line of contact with the first and second connecting rods.

14. An intracorporeal device of any of claims 1, 6 or 7, wherein the internal shaft seat forms a continuous curved surface that circumscribes a perimeter of a portion of the internal shaft.

15. An intracorporeal device of any one of claims 1, 6 or 7, wherein opposing ends of each of the first and second connecting rods are coupled to the static member.

16. An intracorporeal device of claim 15, wherein the first and second connecting rods engage the internal shaft seat.

17. An intracorporeal device of any of claims 1 or 6, wherein the static member is generally cylindrical and has the first and second slots for receiving the first and second connecting rods arranged transverse to the longitudinal axis of the catheter.

* * * * *